United States Patent
Measamer et al.

(10) Patent No.: US 6,168,605 B1
(45) Date of Patent: Jan. 2, 2001

(54) CURVED LAPAROSCOPIC SCISSOR HAVING ARCS OF CURVATURE

(75) Inventors: John P. Measamer; Robert L. Koch, Jr., both of Cincinnati; Narinderjit S. Sambi, Mason, all of OH (US)

(73) Assignee: Ethicon Endo-Surgery, Inc., Cincinnati, OH (US)

( * ) Notice: Under 35 U.S.C. 154(b), the term of this patent shall be extended for 0 days.

(21) Appl. No.: 09/350,079

(22) Filed: Jul. 8, 1999

(51) Int. Cl.$^7$ .................................................. A61B 17/32
(52) U.S. Cl. ............................................. 606/174; 606/170
(58) Field of Search ................................ 606/1, 170, 174, 606/205–210; 600/564

(56) References Cited

U.S. PATENT DOCUMENTS

| | | |
|---|---|---|
| 1,956,588 | 5/1934 | Parker et al. . |
| 3,562,908 | 2/1971 | Rogers . |
| 4,420,884 | 12/1983 | Hembling . |
| 5,312,434 * | 5/1994 | Craininch .......................... 606/174 |
| 5,320,636 | 6/1994 | Slater . |
| 5,478,347 | 12/1995 | Aranyi . |
| 6,001,096 * | 12/1999 | Bissinger et al. .................... 606/174 |

* cited by examiner

*Primary Examiner*—Michael Buiz
*Assistant Examiner*—William Lewis (57) ABSTRACT

A laparoscopic surgical scissors for cutting tissue is disclosed. The laparoscopic surgical scissors has a handle body assembly having an actuation member moveable toward and away from the handle body assembly. An elongated shaft having a proximal and a distal end that define a longitudinal axis is connected to the handle body assembly at the proximal end of said shaft. A pair of cutting blades have a first blade member and a second blade member that are co-operably connected about a common pivot member adjacent to the distal end of the elongated shaft. The common pivot member defines a common pivot axis perpendicular to the elongated shaft. The first blade member has a first cutting edge and the second blade member has a second cutting edge facing the first cutting edge. The blade members have a single point of blade contact translating proximally and distally as the blade members open and close in response to movement of the actuation member away from and toward the handle body assembly. Each of the blade members defines a curvature along the shaft longitudinal axis and each of the curvatures has a proximal end and a distal end. A proximal arc of curvature and a distal arc of curvature define the curvature of each of the blade members.

11 Claims, 8 Drawing Sheets

CURVED LAPAROSCOPIC SCISSOR HAVING ARCS OF CURVATURE

FIELD OF THE INVENTION

The present invention relates, in general, to handheld surgical instruments and, more particularly, to a new and useful handheld surgical cutting instrument having scissor blade members formed with two arcs of curvature.

BACKGROUND OF THE INVENTION

Hand held surgical instruments are well known in the surgical community and have been used for centuries. Many of these instruments have been used for grasping, dissecting, cutting, ligating, or fastening objects to the body. Of interest are hand held surgical cutting instruments such as scissors that are used to cut tissue during a surgical procedure. Scissors are well known in the art and generally consist of a pair of blade members having inner opposed cutting edges that are co-operably connected about a common pivot member. Of special interest are hand held surgical cutting instruments that are adapted to operate laparoscopically, that is, in a minimally invasive surgical procedure wherein the surgery is performed through a small number of small diameter surgical access ports rather than through a large opening or incision within the patient.

In a typical laparoscopic surgery, the abdominal cavity is insufflated with an inert gas and surgical access ports are inserted into the patient. Laparoscopic scissors are inserted into the access ports and the surgical procedure is performed through these access ports. Laparoscopic surgery is sometimes referred to as "keyhole surgery" wherein the access ports are the "keyholes" through which the surgery is performed. As a consequence of the access port ("keyhole") size, laparoscopic scissors are characterized by a pair of scissor-like handles, a small diameter elongated shaft that forms a gas tight seal with the access port, and a small scissors end effector that is operatively coupled with at least one of the handles. Many laparoscopic scissors are curved to provide better visibility during laparoscopic surgery and to provide an improved angle of attack for electrocautery.

Laparoscopic scissors instruments are frequently provided with an electrocautery pin that can be operatively coupled to a RF electrosurgical generator by a connector cable. The RF generator provides both a cutting and a coagulating RF waveform that can be applied to tissue with either the cutting edges of the blades (to reduce bleeders during cutting) or with the outside of the flat faces of the curved scissors blades during spot coagulation. As mentioned above, the angle of attack of the curved scissors blades provides a definite benefit over conventional straight scissors blades when performing spot coagulation.

Surgical scissors instruments face an exceptionally daunting task as they must provide a good clean cut in a wide variety of tissue types that can range from a "soft" tissue such as liver tissue, to a tough resilient tissue such as peritoneum or ligaments. During open and laparoscopic surgery, it is important to provide surgeons with scissors instruments that continuously provide good cutting action throughout the surgical procedure, and that the cutting action does not deteriorate with use. Instruments that do not exhibit good cutting action generally produce partial cuts. The portion of the tissue that is not cut is generally pinched between the blades and can become crushed or damaged. The portion of uncut tissue is frequently referred to as a "tissue tag".

Two factors affect the cutting ability of a surgical scissors instrument—the sharpness of the cutting edges of the blade members and the ability to preload or bias the cutting edges of the blade members together. When the cutting edges are biased together, they produce a single moving point of cutting edge contact as the blades close. Like a dull knife, dull blade members have difficulty cutting tissue and frequently produce a partial cut. Even when the dull blade members are adequately biased together during the cutting stroke, the dull blade members can pinch or wedge uncut tissue between the blade members and splay or spread the blade member tips apart. Producing sharp scissors blades is well known in the art and future discussions will be limited to biasing the cutting edges together.

When the cutting edges of the blade members are not adequately biased together, the scissors blades easily splay or spread apart. When this happens, the moving point of contact between the cutting edges of the scissors blades is broken and the surgical scissors instrument may not cut. Holding the blade members together is well known in the art and has generally been addressed in the following three general ways: a) camming the blade members, b) forming the blade members with a longitudinal bow or bend, and c) holding or biasing the blades tightly together at the pivot member. These methods have been used singly and in combination.

Camming the blade members generally involves the addition of a cam surface proximal to the pivot member and on the inside surface of each blade member. The pivot member holds the blade members together and as the blade members close, the cam surfaces bias the portions of the blade members proximal to the pivot member apart and the portions of the blade members distal to the pivot member together. Thus, the proximal cam surfaces effectively bias the distal cutting edges of the blade members together to produce a single moving point of blade contact. Camming the blade members together is well known in conventional scissors art and was described by M. Parker et al. in U.S. Pat. No. 1,956,588. Parker et al. teaches the use of a pivot pin to hold the blade members together.

Whereas the cams used in the conventional scissors described by Parker et al. were indeed revolutionary, they were costly. William Hembling in his U.S. Pat. No. 4,420,884 described forming the blade members by progressively stamping sheet metal to produce a control cam proximal to the pivot member to bias the cutting edges together, and an arcuate blade cross section to produce the effect of hollow grinding. Hembling's invention described camming the blade members together in the manner of M. Parker et al. but at a much lower cost. The blade members were held together in the manner of Parker et al.

Although the use of cams to bias conventional non-surgical scissors together was historically well known, the use of cams in laparoscopic surgery was not. Charles Slater in his U.S. Pat. No. 5,320,636 describes the use of cams proximal to the pivot member to bias the distal cutting edges together. Slater also discloses progressive biasing wherein the greatest bias force is applied when the blade members are open and progressively less bias is applied as the blade members close.

Whereas camming the cutting edges of the blade members together did indeed provide a distal bias force on the cutting edges of the blade members, it was still possible to splay the distal ends of the blade members. This was especially noticeable on long blades formed from a thin material such as sheet metal. What was needed was a different method of biasing the blade members together that was more resistant to splaying and, if desired, used in combination with the cams described previously. Such a method is the application of a longitudinal bow or bend to at least one of the blade members. The longitudinal bend is applied to the blade distal to the pivot member and has little or no effect on biasing the proximal portion of the cutting edges together when the blade members are open. As the blade members are closed, the longitudinal bends generally bring a central and a distal portion of the cutting edges into contact. As the blades are closed, the bias force increases and rises to a maximum when the blades are fully closed. This effect is especially useful for long thin blades where as the blades are closed, the increasing bias force helps counteract the increasing deflection caused by the distally moving point of cutting edge contact. The blade members can be overbent, a term that is used to describe when the tip of one blade member is bent over or beyond the outside of the tip of the other blade member. A pair of blades that are overbent will produce a higher bias force than a pair of blade members that are not overbent. The lateral bending of the blade members is taught in the previously described U.S. Pat. No. 5,320,636 by Slater. Hembling teaches overbent conventional scissors blade members in the previously described U.S. Pat. No 4,420,884.

As described above, biasing the blades tightly together at the pivot member is the third method of holding the blade members together and this can have a definite effect on the cutting abilities of the proximal portions of the blade members. Holding the scissors members tightly together at the pivot is often accomplished by using a portion of the pivot member to bias the blades together. The pivot member is frequently a fastener such as a pin, a rivet, or a shoulder screw that can bias the cutting edges of the blades together. If the fastener does not adequately bias the blades together initially, or loosens during operation, the scissors blades will not have good cutting action. A rivet as a fastening and pivot means for a garden shear was described in U.S. Pat. No. 3,562,908 by E. A. Rogers.

Figure 4:
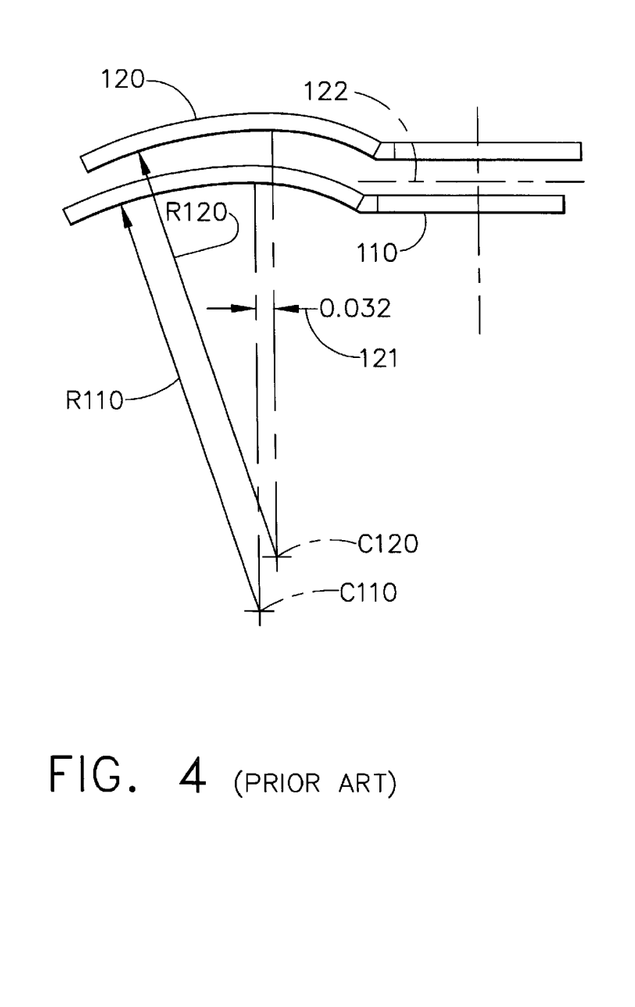
FIG. 4 is a top view of a pair of prior art scissor blades showing the geometry used to describe the scissors blades.

As mentioned above, laparoscopic scissors instruments frequently have curved blade members to enhance visibility of the blade members through a laparoscope and to provide a surface for spot coagulation. Without the curved blade members, it can be very difficult to identify the cutting location during laparoscopic surgery. U.S. Pat. No. 5,478,347 was issued to Aryani describing a pair of curved blade members 110 and 120. The prior art blade members 110,120 are shown in FIG. 4 and are described as being crescent in shape and preferably having a different radii of curvature R110, R120 respectively for blade members 110,120 relative to the pivot point. When the blade members are assembled, the center of the radius of curvature C110 of blade member 110 is offset from a center of the radius of curvature C120 by a predetermined distance such that the blade members 110,120 contact each other during opening and closing. This is said to enhance the shearing effect of the scissors and to reduce the incidences of the blades splaying during cutting.

The single radius of curvature described in Aryani did not directly address the need to enhance the biasing of the proximal portion of the cutting edges together as the jaw members close. What is needed is a pair of opposed blade members having a pair of proximal arcs of curvature and a pair of distal arcs of curvature, each pair of arcs of curvature providing a biasing force best suited for cutting with that portion of the cutting edges of the blade members.

SUMMARY OF THE INVENTION

The present invention is a laparoscopic surgical scissors having a handle body assembly and an actuation member moveable toward and away from the handle body assembly. An elongated shaft defines a shaft longitudinal axis and has a proximal end and a distal end. The elongated shaft is connected to the handle body assembly at the proximal end of the shaft.

A pair of cutting blades having a first blade member and a second blade member are co-operably connected about a common pivot member adjacent to the distal end of said elongated shaft. The common pivot member defines a common pivot axis perpendicular to said elongated shaft. The first blade member has a first cutting edge and the second blade member has a second cutting edge facing the first cutting edge. The blade members have a single point of blade contact translating proximally and distally as the blade members open and close in response to movement of the actuation member away from and toward the handle body assembly. Each of the blade members define a curvature along the shaft longitudinal axis and each of the curvatures have a proximal end and a distal end.

The curvature of the blade members is defined by a proximal arc of curvature and a distal arc of curvature. The proximal arc of the first blade member has a first radius of curvature and the distal arc of the first blade member has a second radius of curvature. The proximal arc of the second blade member has a third radius of curvature and the distal arc of the second blade member has a fourth radius of curvature. Each of the radii of curvature is taken through a common centerline parallel to the common pivot axis, and each of the radii of curvature being different from each other.

Significantly, the novel laparoscopic surgical scissors for cutting tissue during a surgical procedure provides the surgeon with a pair of scissor blade members that provide enhanced cutting. That is, the novel scissors blade members are defined by a pair of proximal arcs of curvature and a pair of distal arcs of curvature. Each pair of arcs of curvature bias the cutting edges together with a biasing force that is best suited for cutting with that portion of the blade members. As the blade members close, a single moving point of contact is maintained between the cutting edges—along with a changing bias force. Consequently, the surgeon is provided with good cutting action with the proximal portions of the blade members, with the distal portions of the blade members, and all points in between.

The proximal and distal arcs of curvature of the laparoscopic scissors instrument of this invention are formed such that they provide an even feel throughout the entire cutting range. The proximal arcs of curvature are overbent to prevent splaying of the tips of the blades as they cut. The proximal and distal portions of the blade members meet at the point of blade tangency to provide a smooth cutting transition from proximal arcs of curvature to the distal arcs of curvature. Additionally, the curved blades provide enhanced visibility of the blade members in a laparoscopic environment.

Furthermore, connection of the laparoscopic scissors instrument of the preferred invention to a RF generator provides the user with the ability to apply RF energy to tissue with the blade members. During the cutting stroke, the application of RF energy from the cutting edges of the blade members cauterizes the adjacent tissue. This type of electrocautery staunches potential bleeders and provides bloodless cuts. In the event of a bleeder, the curved shape of the blade members is especially useful for spot coagulation.

The various features of novelty which characterize the invention are pointed out with particularity in the claims annexed to and forming a part of the disclosure. For a better understanding of the invention, reference is made to the accompanying drawings and descriptive matter in which the preferred embodiments of the invention are illustrated.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The preferred embodiment of the present invention is a hand held surgical scissors instrument for cutting tissue during a laparoscopic surgical procedure. In particular, the present invention is a laparoscopic surgical scissors instrument having scissor blade members formed with two arcs of curvature. The scissors blade members are formed from a pair of proximal arcs of curvature and a pair of distal arcs of curvature. These arcs of curvature bias the cutting edges of the blade members together at a single point of moving contact with a biasing force that is best suited for cutting with that portion of the blade members. The surgical scissors instrument 30 of the preferred invention is shown in FIGS. 1–3 and FIGS. 5–12.

Figure 1:
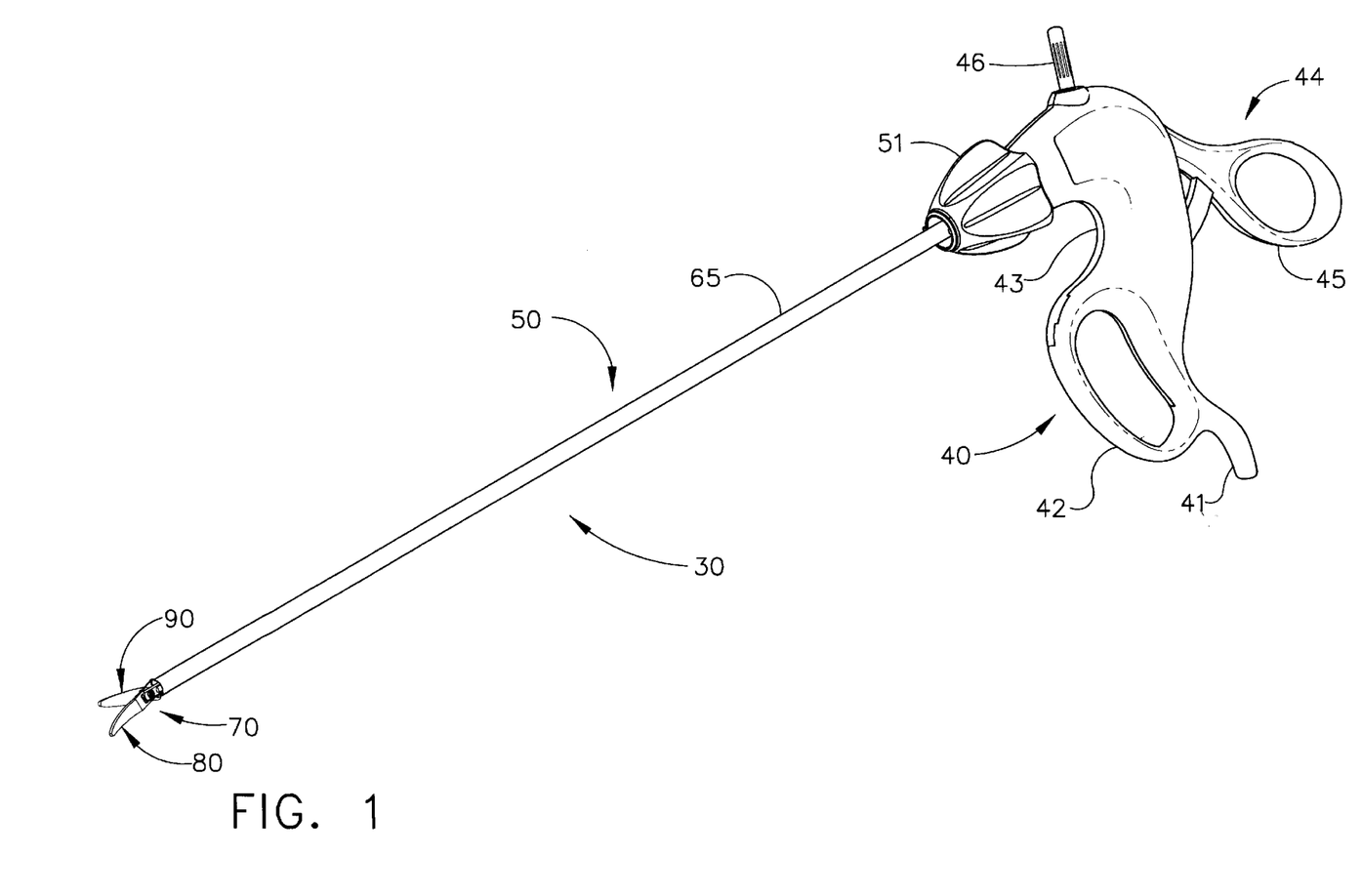
FIG. 1 is an isometric view of the preferred handheld surgical scissors instrument of this invention having scissor blade members formed with two arcs of curvature.

FIG. 1 shows an isometric view of the surgical scissors instrument 30 of the preferred invention. The laparoscopic scissors instrument has a proximal handle body assembly 40 for the surgeon to grasp, an elongated shaft assembly 50 rotatably connected to the handle body assembly 40, and an end effector 70 attached to the distal end of the elongated shaft assembly 50. It is an object of the invention to provide a universal surgical instrument that can be assembled with a wide variety of end effectors of different sizes, shapes and uses. The handle body assembly 40 is ergonomic in design having an arcuate finger hook 41 for the little finger, a finger loop 42 for the two center fingers, and a finger rest 43 for the index finger. A moveable actuation member 44 has an actuation loop 45 for the thumb and is operably connected to the end effector 70. Movement of the actuation member 44 towards and away from the finger loop 42 closes and opens the end effector 70. A single pair of scissors blades, first and second blade members 80 and 90 will be used throughout the description below. The elongated shaft assembly 50 is fixably and rotatably attached within a distal end of the handle body assembly 40. A rotation knob 51 is provided to rotate the elongated shaft assembly 50 and the first and second blade members 80 and 90. A cautery pin 46 extends from the handle body assembly 40 and is electrically connectable to a RF generator (not shown).

Figure 2:
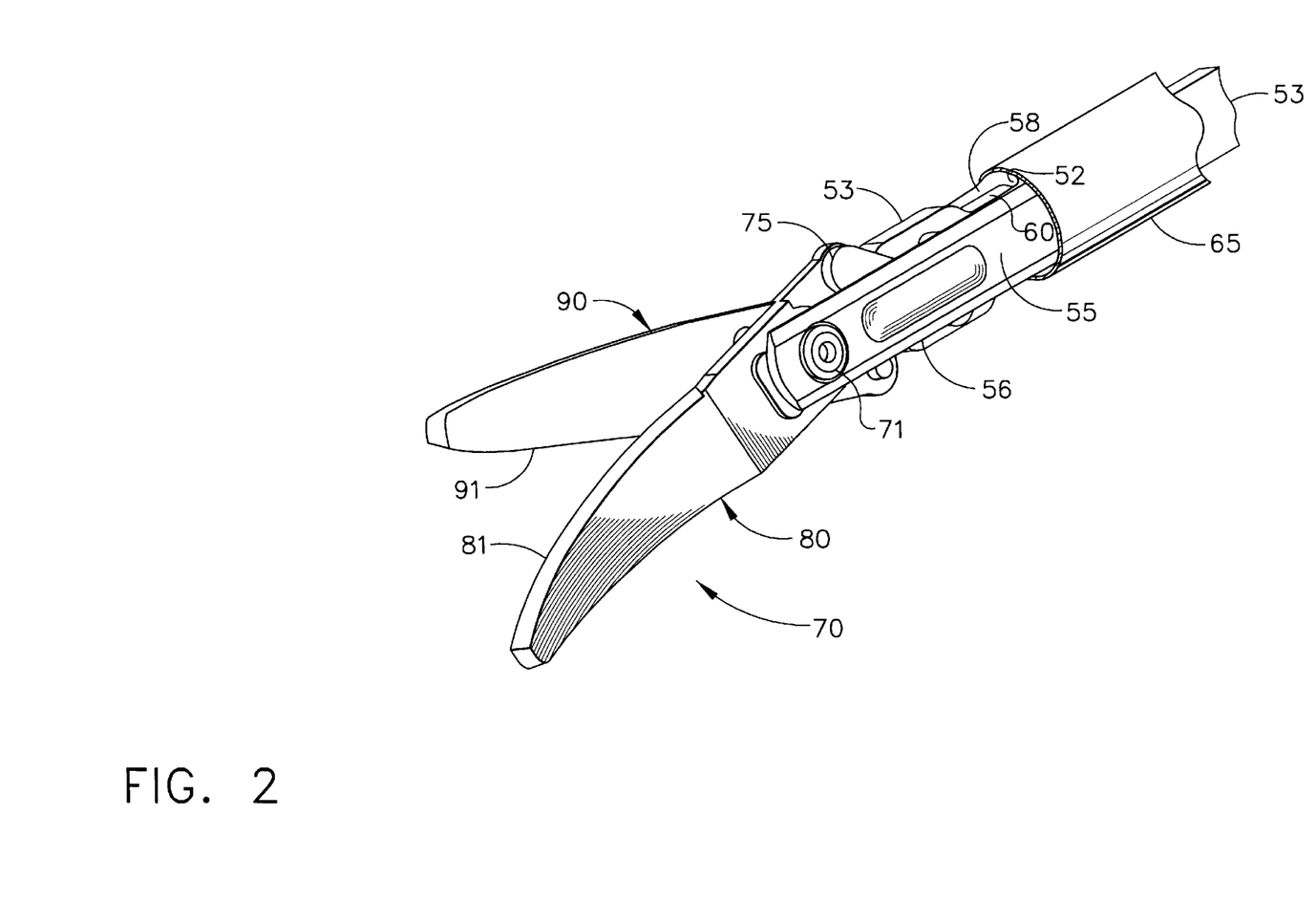
FIG. 2 is an isometric view of the end effector of the surgical scissors instrument of FIG. 1.

FIG. 2 shows a partial isometric view of the distal end of the end effector 70 of the surgical scissors instrument 30 (FIG. 1). First and second blade members 80 and 90 of the preferred invention are shown partially opened and mounted within a clevis 55. A first cutting edge 81 and a second cutting edge 91 are opposedly located on the inside of first and second blade members 80 and 90. First and second blade members 80 and 90 rotate or pivot about a pivot member 71 that is perpendicular to a longitudinal axis of the surgical scissors instrument 30. The pivot member 71 extends through a first fork member 56 and a second fork member 58 of the clevis 55. The first fork member 56 and a second fork member 58 extend from a distal end of an elongated shaft 52 that is rotatably attached to the handle body assembly 40 (FIG. 1). An actuation rod 53 is coaxialy located and moveable within elongated shaft 52 and is operably connected to a pair of links 75 of the end effector 70. The links 75 operably connect the actuation rod 53 to the blade members 80 and 90 such that distal and proximal motion of the actuation rod 53 open and close the blade members 80 and 90. Insulation material 65 is applied over the elongated shaft 52 to protect the surgeon and the patient during the use of electrocautery (shown partially removed for clarity).

Figure 3:
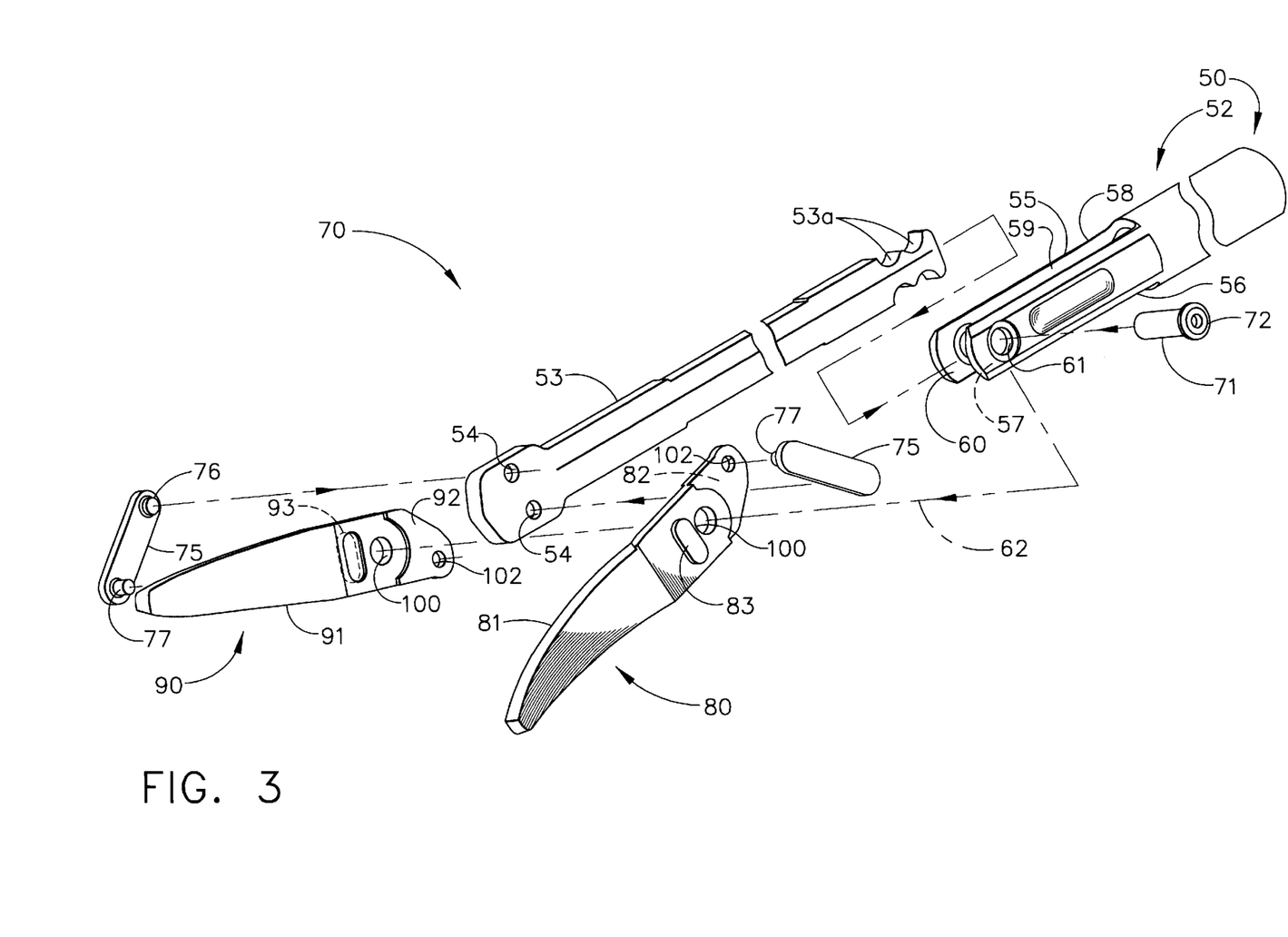
FIG. 3 is an exploded isometric view showing all of the elements of the end effector illustrated in FIG. 2 in exploded form.

FIG. 3 is an isometric view showing all of the components of FIG. 2 in exploded form. The individual elements will now be described along with their assembly. The backbone of the elongated shaft assembly 50 is an elongated shaft 52 formed from a thin sheet of surgical grade metal. The elongated shaft 52 is not formed in the conventional manner wherein a stainless steel tube is fabricated to form elongated shaft 52, but is formed from a flat sheet in a series of forming dies such as a progressive stamping and forming die. The flat sheet of steel is curled or formed into a hollow elongated shaft 52 having a cylindrical cross section, and the first and second fork members 56 and 58 of clevis 55. A pivot bore 61 is spaced proximally from a distal end of the fork members 56 and 58 of the clevis 55 and extends therethrough. The pivot bore 61 is perpendicular to a longitudinal axis of the shaft and forms a pivot axis 62.

The actuation rod 53 is an elongated member that is movably located within the elongated shaft 52 and is operably coupled to the end effector 70 and the actuation member 44. Actuation rod 53 is preferably formed as, but not limited to, a stamping. The actuation rod 53 has two pairs of notches 53a located at the proximal end and a pair of rod bores 54 near the distal end extending therethrough. The notches 53a are operably coupled to the actuation member 44 and the rod bores 54 receive the links 75. The links 75 are generally a flat plate having a rod pin 76 and a blade pin 77 extending therefrom and are preferably stamped or formed from a single piece of material. The pins 76 and 77 are spaced apart and parallel. The rod pin 76 is receivable within the rod bores 54 as shown. The blade pin 77 pivotably mounts within a blade pin bore 102 extending therethrough each blade member 80 and 90.

The first and second blade members 80 and 90 are generally parallel and have three distinct portions, a distal curved portion along the first cutting edge 81 and 91, a central pivot portion having a blade bore 100 extending therethrough, and a distal portion having a first and a second heel surface 82 and 92. The distal curved portion of the blade members 80 and 90 have adjacent first and second cutting edges 81 and 91. The blade bores 100 of the first and second blade members 80 and 90 define a common pivot axis 62. First and second heel surface 82 and 92 are offset inwardly towards the opposite blade and have the blade pin bore 102 extending therethrough. A first and a second clevis contact surface 83 and 93 opposed and extends outwardly between the distal curved portion and the blade bore 100 of each blade member 80 and 90.

Figure 7:
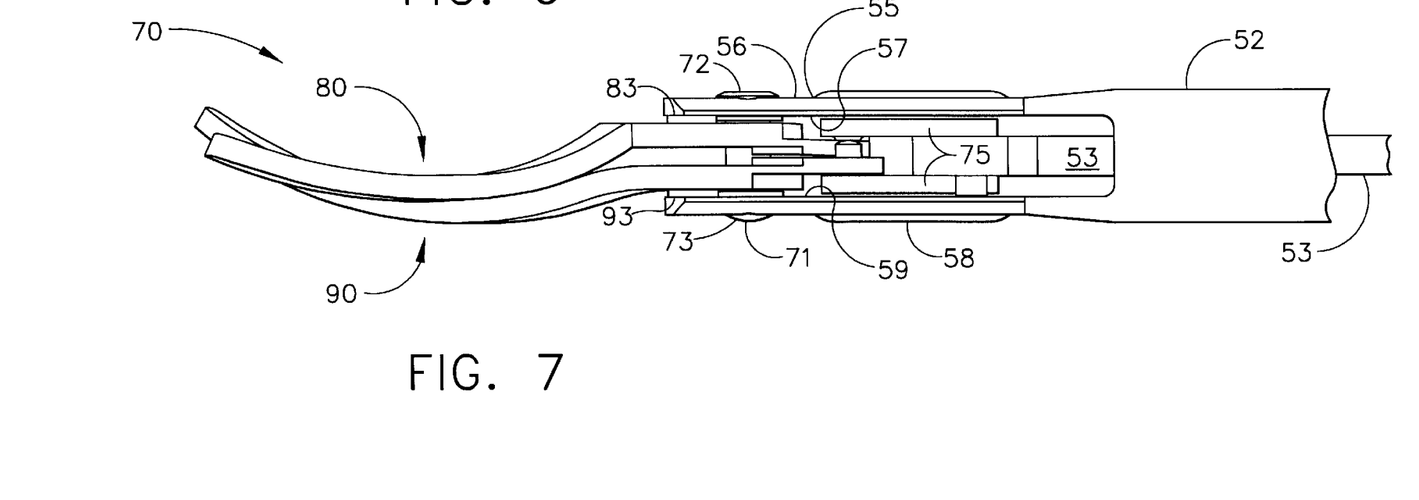
FIG. 7 is a bottom view of the end effector of the preferred handheld surgical scissors instrument of FIG. 1 showing the different arcs of curvature of the scissors blades when the scissors blades are open.

First and second blade members 80 and 90 are co-operably connected about a common pivot member 71 that is generally cylindrical in form and has a preformed head 72 at one end. The to blade members 80 and 90 are initially captured within the clevis 55 by the placement of the pivot member 71 within the pivot bore 61 of fork members 56 and 58 and the blade bore 100 of the first and second blade members 80 and 90. To complete the capture of the blade members 80 and 90 within the clevis 55, the unformed end of the pivot member is riveted or formed into a formed head 73 (FIG. 7). This final assembly biases the blade members 80 and 90 together to prevent splaying of the blades when they are subjected to a lateral tissue load.

The formed head 73 of the pivot member 71 is formed in a process that preloads the blade members 80 and 90 together. The blade members 80 and 90 are moved to the closed position, and the end effector 70 is placed within a special a nest within a riveting fixture (not shown) having a load cell. The load cell is positioned to contact the outside of the clevis 55 on the side that is opposite to the head 72 of the inserted pivot member 71. Specifically, the contact point is on the clevis directly adjacent to the clevis contact surface 83 or 93 of the blade member 80 or 90. A predetermined load is applied to the head 72 of the pivot member to force the end effector 70 against the load cell. This loading biases the first and second fork members 56 and 58 and the blade members 80 and 90 inwardly at an increasing pressure until the adjacent load cell reads a load of between 8 to 15 pounds but most preferably 13 pounds. The final step of the assembly process is to bring an orbital riveter into contact with the unformed end of pivot member 71 (adjacent to the load cell) to create a formed head 73 (FIG. 7). As the rotary riveter is applied to the pivot member 71 the formed head 73 removes load from the load cell. Upon attaining the appropriate predetermined loading, the process stops and the completed end effector 70 is removed from the riveting fixture. The first and second fork members 56 and 58 are permanently biased inwardly into contact with the blade members 80 and 90 by the opposing heads of the pivot member 71 at the force range described above.

FIG. 4 is an illustration of curved blade prior art showing the geometry used to form a third and a fourth blade member 110 and 120. The prior art third blade member 110 has a radius of curvature R110 and a fourth blade member 120 has a radius of curvature R120. A center of radius of curvature of the third blade 110 is offset 121 a predetermined distance (such as 0.032) along a longitudinal axis 122 from a center of a radius of curvature of the fourth blade 120.

Figure 5:
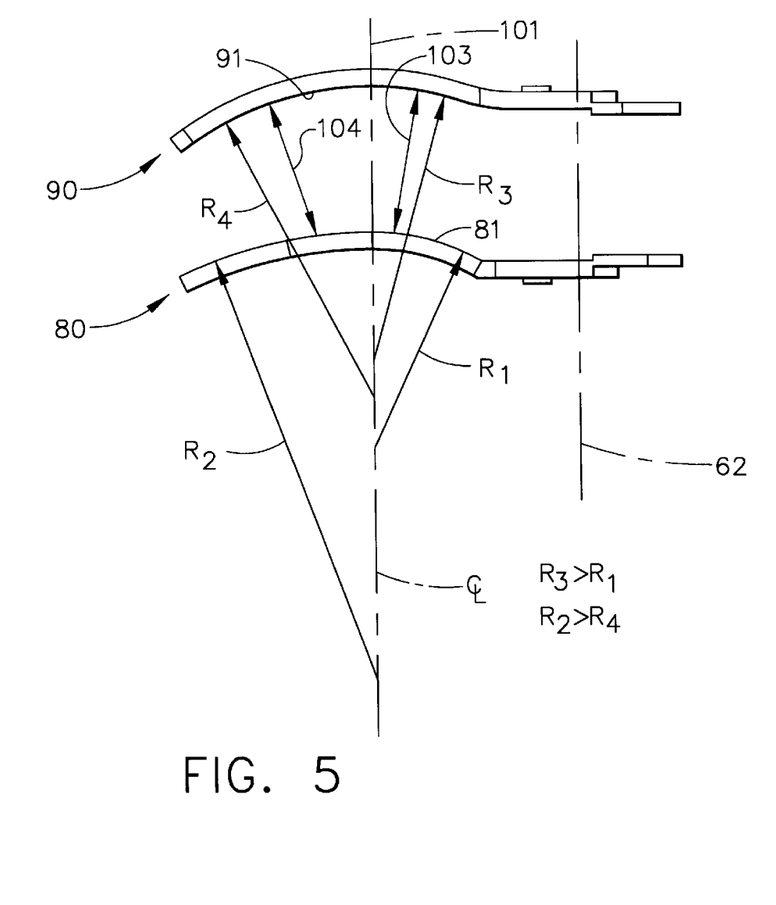
FIG. 5 is a top view of a pair of scissor blades of the preferred handheld surgical scissors instrument of FIG. 1 showing the geometry used to describe the scissors blades.

FIG. 5 shows the geometry used to describe a pair of curved blade members of the present invention. The first and the second blade members 80 and 90 have a proximal arc of curvature 103 and a distal arc of curvature 104. The proximal arc of curvature 103 of the first blade member 80 has a first radius of curvature R1 and the proximal arc of curvature 103 of the first second blade member 90 has a third radius of curvature R3. The distal arc of curvature 104 of said first blade member 80 has a second radius of curvature R2 and the distal arc of curvature 104 of the second blade member 90 has a fourth radius of curvature R4. It is of note that each of the radii of curvature is being taken through a common centerline 101 parallel to the common pivot axis 62. It is also of note that each of the radii of curvature are different from each other and that R3 is greater than R1 and that R2 is greater than R4. This means that the proximal radii are such that the proximal portion of the second blade member 90 is curved towards the first blade member 80 and the distal portion of the second blade member 90 is curved towards the first blade member 80. The curves are such that the second blade member 90 or outer blade overbends the inner first blade member 80 as evidenced by the blade tips shown in the bottom view of FIG. 7. The overbending ensures a single moving point of cutting edge contact is maintained as the blade members 80 and 90 close and ensures that the blade members 80, 90 remain together when subjected to a lateral tissue load. Preferably, R1 is about 0.390 inches, R2 is about 0.800 inches, R3 is about 0.493 inches, and R4 is about 0.562 inches.

Defining the proximal and distal portions of each blade member 80 and 90 with a proximal arc of curvature 103 and a distal arc of curvature 104 offers distinct advantages. The distal portions of the blade members 80 and 90 require a different bias force than the proximal portions. The distal portions of the blade members 80 and 90 are relatively long and flexible and deflect more in the lateral direction from a given tissue load than the proximal portions of the blade members 80 and 90. The proximal portions of the blade are shorter and deflect less. Thus, the distal portions of the blade members 80, 90 need a larger biasing force to counteract the greater deflection at the distal portions of the blade members 80 and 90 than the proximal portions of the blade members 80, 90. Applying the same biasing force to the proximal portion of the blade members 80, 90 can cause smearing or rolling of the cutting edges 81 and 91 (FIG. 2). The two arcs of curvature 103, 104 provide two different biasing forces that are optimal for each portion of the blade.

Figure 6:
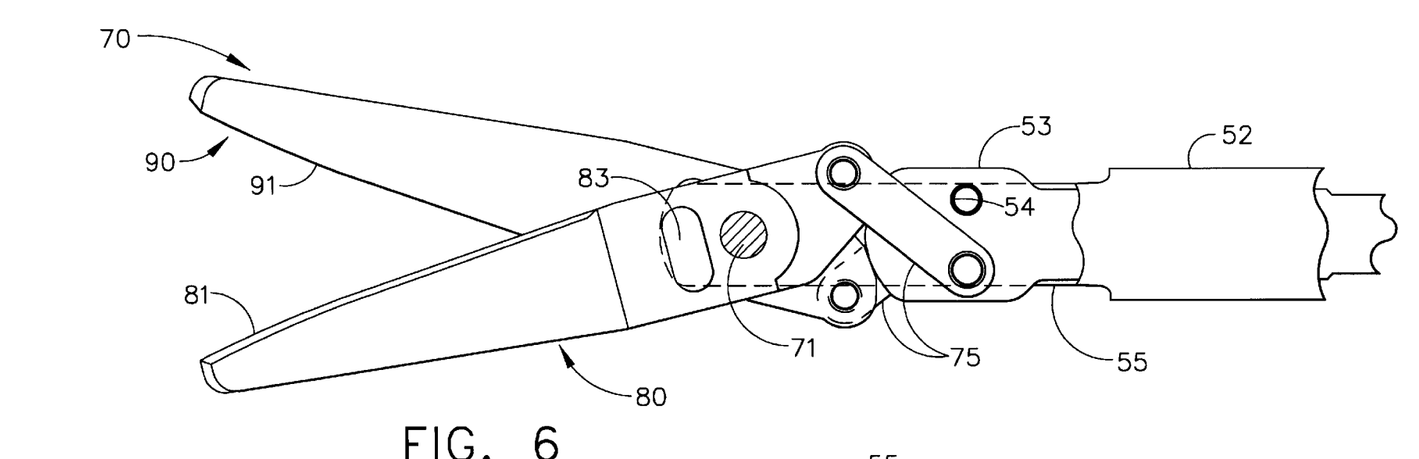
FIG. 6 a side view of the end effector of the preferred handheld surgical scissors instrument of FIG. 1 with a portion of a clevis removed to show the positions of the elements of the end effector when the scissors blades are open.
Figure 8:
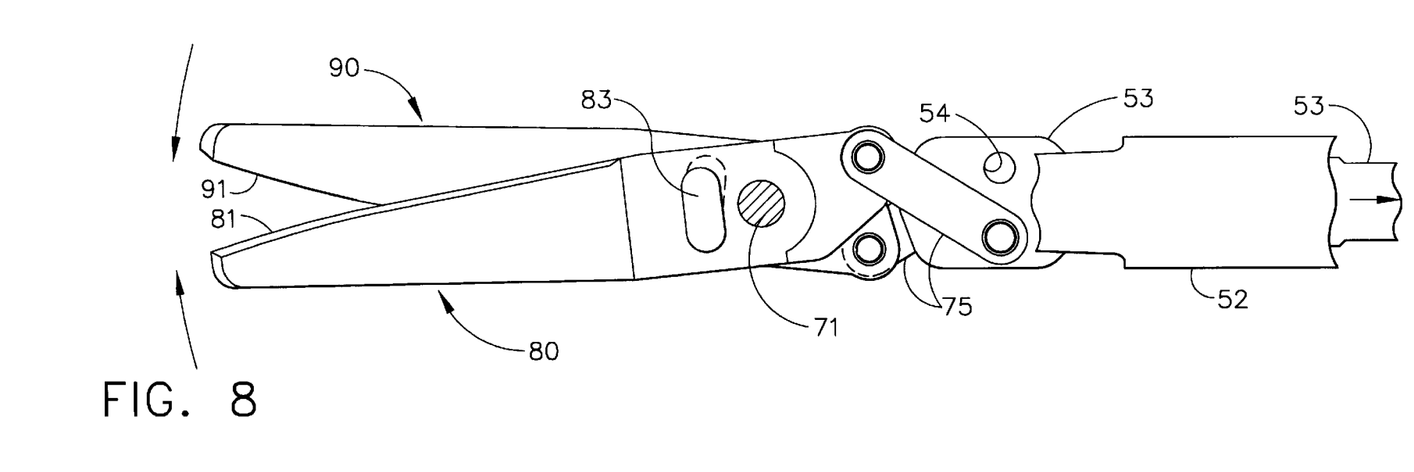
FIG. 8 a side view of the end effector of the preferred handheld surgical scissors instrument of FIG. 1 with a portion of a clevis removed to show the positions of the elements of the end effector when the scissors blades are partially closed.
Figure 9:
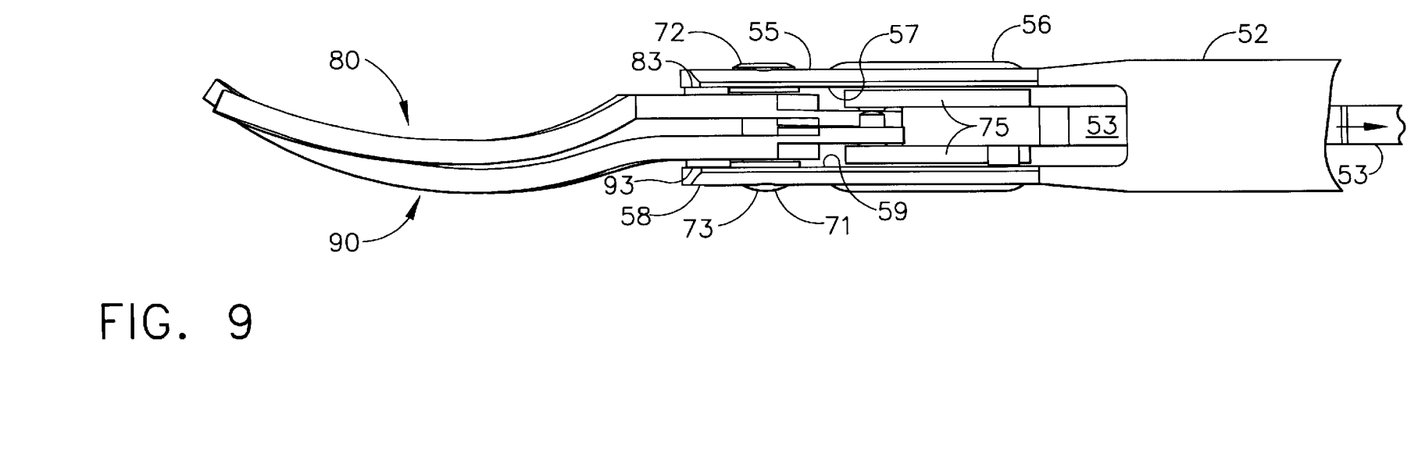
FIG. 9 is a bottom view of the end effector of the preferred handheld surgical scissors instrument of FIG. 1 showing the different arcs of curvature of the scissors blades when the scissors blades are partially closed.
Figure 10:
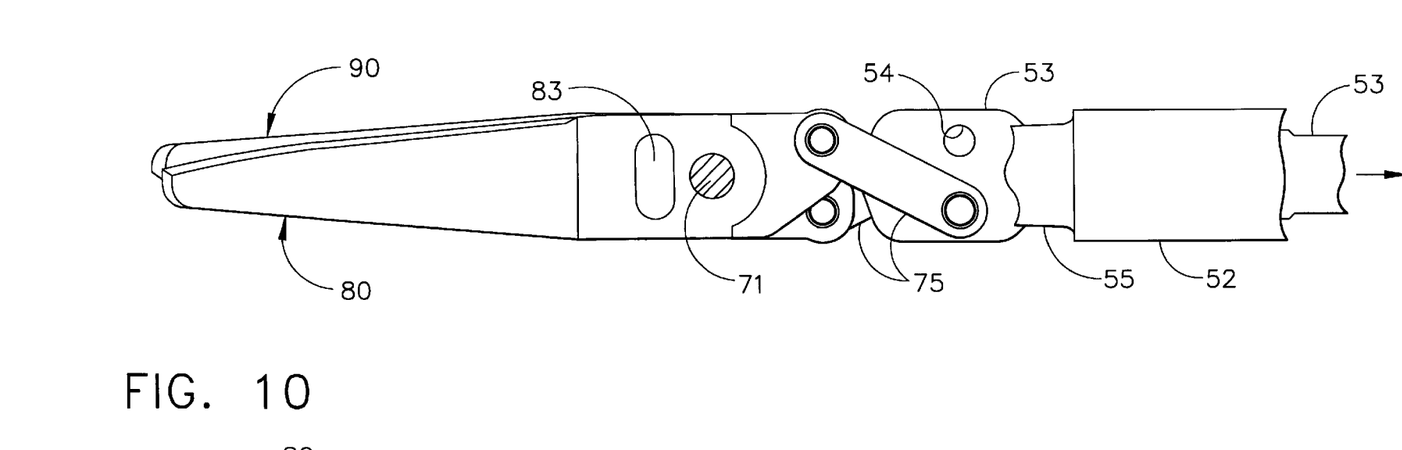
FIG. 10 a side view of the end effector of the preferred handheld surgical scissors instrument of FIG. 1 with a portion of a clevis removed to show the positions of the elements of the end effector when the scissors blades are fully closed.
Figure 11:
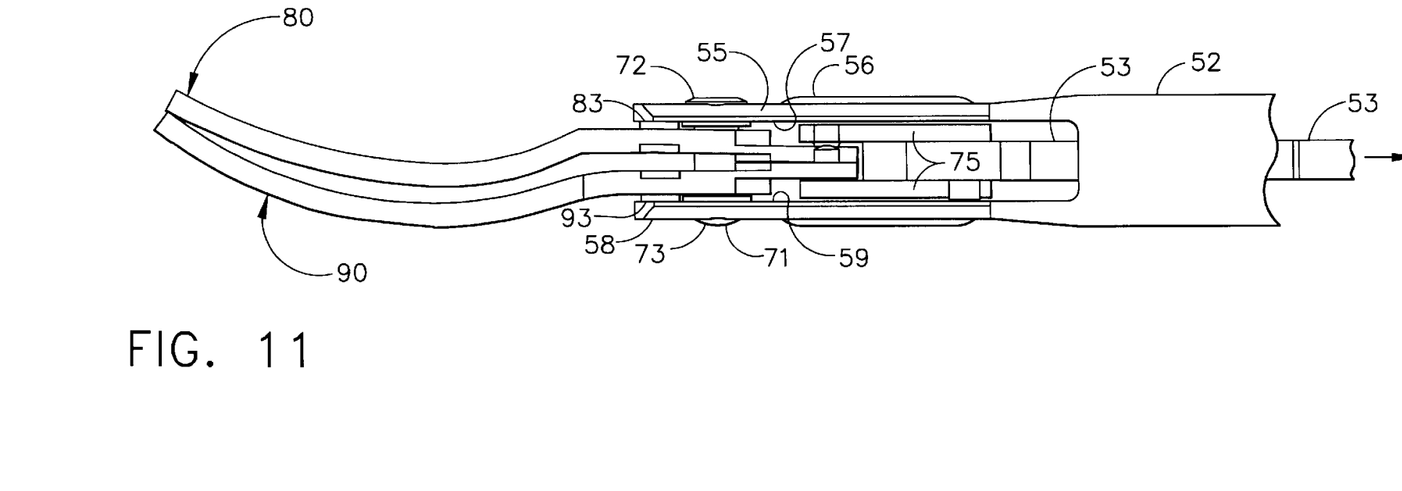
FIG. 11 is a bottom view of the end effector of the preferred handheld surgical scissors instrument of FIG. 1 showing the different arcs of curvature of the scissors blades when the scissors blades are fully closed.

FIGS. 6–11 show the steps in closing the end effector 70 of the surgical scissors instrument. More particularly, FIGS. 6 and 7 show the end effector with the blade members 80 and 90 fully open, FIGS. 8 and 9 show the blade members 80, 90 partially closed, and FIGS. 10 and 11 show the blade members 80, 90 fully closed. FIG. 6 is a side view of the end effector 70 and FIG. 7 is a bottom view of FIG. 6.

FIGS. 6 and 7 show the positions of the elements of the end effector 70 and the distal portions of the elements of the elongated shaft assembly 50 (FIG. 1). A portion of the first fork member 56 of the clevis 55 is removed from FIG. 6 to show the components within. The blade members 80 and 90 are pivoted open around the pivot member 71 and the first and second cutting edges 81 and 91 are engaged. The clevis contact surfaces 83 and 93 are in contact with the first and the second inner fork surfaces 57 and 59 and bias the blade members 80 and 90 together. The proximal portion of the blade members 80 and 90 are spread apart and the attached links 75 are angled as shown.

In FIG. 7, the reader is advised to note the overbending of the second jaw member 90 relative to the first jaw member 80. This overbending reduces splaying from tissue loads and ensures that as the blade members 80 and 90 close, they deflect outwardly away from each other to maintain a single moving point of contact between the first cutting edge 81 and second cutting edge 91. FIG. 7 shows the head 72 and a formed head 73 biasing the first fork member 56 and the second fork member 58 inwardly. The first and second inner fork surfaces 57 and 59 of the first and second fork members 56 and 58 contact the blade members 80 and 90 at first and second clevis contact surfaces 83 and 93 with a bias force between 8 to 15 pounds. It is most preferable that the bias force is 13 pounds. The clevis contact surfaces 83 and 93 are located distal to the pivot member 71 and are the only points of contact between the blade members 80 and 90 and the clevis 55.

In FIGS. 8 and 9, the blade members 80, 90 are shown partially closed. The actuation rod 53 is moving proximally (to the right) and is pulling on the links 75 to close the blade members 80 and 90 together. The point of contact between the first and second cutting edge 81 and 91 is moving distally (to the left) from the point of contact as shown in FIG. 6. In FIG. 9, the overbent blade members 80 and 90 are shown deflecting outwardly from the point of cutting edge contact. It is of note that the distal portions of blade members 80 and 90 are overbent and the proximal portions are spaced apart from the point of cutting edge contact.

In FIGS. 10 and 11, the blade members 80 and 90 are fully closed by the proximal motion of the actuation rod 53. This motion has moved the links 75 from the position of FIG, 8 to that of FIG. 10 and fully closed the blade members 80, 90 about the pivot member 71. In FIG. 10 the blade members 80 and 90 are fully closed and the single point of contact is at the blade tips.

Figure 12:
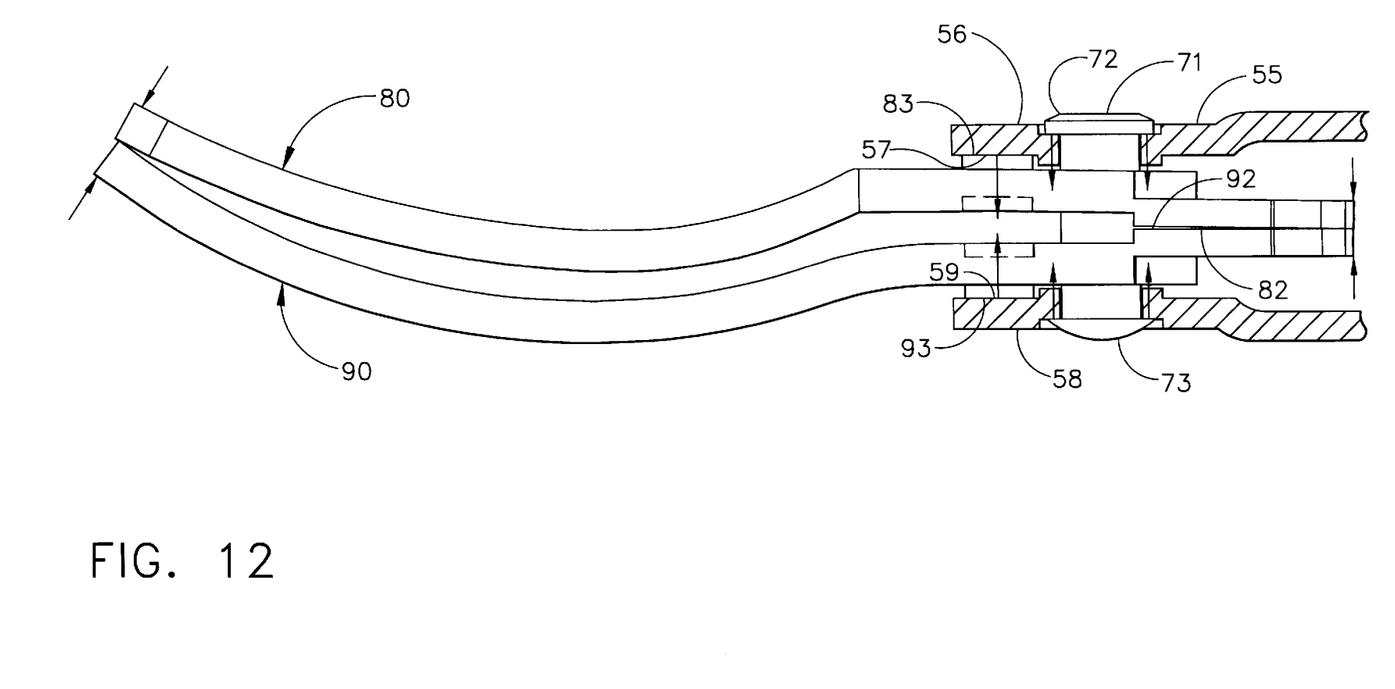
FIG. 12 is a partially sectioned bottom view of the end effector of the preferred handheld surgical scissors instrument of FIG. 1 showing the points of contact of the scissors blades and clevis when the scissors blades are fully closed.

FIG. 12 is a partially sectioned view of the end effector 70 (FIG. 1) of the preferred invention showing the effects of preloading the pivot member. Force vectors are shown showing extending inwards from the head 72 and formed head 73 of the pivot member 71. This inward bias force is applied to the clevis contact surfaces 83 and 93 of the blade members 80 and 90 by the inner fork surfaces 57 and 59 of the clevis 55. This inward bias forces the blade members 80 and 90 together proximally at the blade heel surfaces 82 and 92 and distally at the member blade tips. This bias force prevents the blade tips from splaying apart when they are subjected to a lateral tissue load during cutting.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A laparoscopic surgical scissors comprising:
   a handle body assembly having an actuation member moveable toward and away from said handle body assembly;
   an elongated shaft defining a shaft longitudinal axis, said elongated shaft having a proximal end and a distal end, and said elongated shaft connected to said handle body assembly at the proximal end of said shaft;
   a pair of cutting blades having a first blade member and a second blade member co-operably connected about a common pivot member adjacent to the distal end of said elongated shaft, said common pivot member defining a common pivot axis perpendicular to said elongated shaft, said first blade member having a first cutting edge and said second blade member having a second cutting edge facing said first cutting edge, said blade members having a single point of blade contact translating proximally and distally as said blade members open and close in response to movement of said actuation member away from and toward said handle body assembly, each of said blade members defining a curvature along the shaft longitudinal axis and each of the curvatures having a proximal end and a distal end;
   wherein the curvature of said blade members is defined by a proximal arc of curvature and a distal arc of curvature, said proximal arc of said first blade member having a first radius of curvature and said distal arc of said first blade member having a second radius of curvature, said proximal arc of said second blade member having a third radius of curvature and said distal arc of said second blade member having a fourth radius of curvature, each of the radii of curvature being taken through a common centerline parallel to the common pivot axis and being different from each other, said second radius of curvature of said first blade member being larger than said fourth radius of curvature of said second blade member, and when said first and second blade members are open the ratio of said second radius of curvature of said first blade member to said fourth radius of curvature of said second blade member is between about 1 and about 2.500.

2. The laparoscopic surgical scissors of claim 1 wherein said proximal arc of curvature of each of said blade members extends from the proximal end of the curvature of the blade member to said common centerline.

3. The laparoscopic surgical scissors instrument of claim 2 wherein said distal arc of curvature of each of said blade members extends from said common centerline to the distal end of said curvature of said blade members.

4. The laparoscopic surgical scissors of claim 1 wherein the ratio of said second radius to said fourth radius is between about 1.250 and 1.667.

5. The laparoscopic surgical scissors of claim 6 wherein the preferred ratio of said second radius to said fourth radius is 1.423.

6. The laparoscopic surgical scissors of claim 5 wherein when said first and second blade members are closed, said second radius is smaller than said fourth radius.

7. The laparoscopic surgical scissors of claim 1 wherein as said first and second blade members close, said first blade member deflects inwardly so to decrease said second radius and said second blade member deflects outwardly so to increase said fourth radius.

8. The laparoscopic surgical scissors of claim 1 wherein when said first and second blade members are open, said first radius of curvature of said first blade member is smaller than said third radius of curvature of said second blade member.

9. The laparoscopic surgical scissors of claim 8 wherein when said first and second blade members are open, a ratio of said first radius of curvature of said first blade member to said third radius of curvature of said second blade member is between about 0.999 and about 0.583 inches.

10. The laparoscopic surgical scissors of claim 8 wherein when said first and second blade members are open, the ratio of said first radius to said third radius is between about 0.891 and about 0.691.

11. The laparoscopic surgical scissors of claim 9 wherein when said first and second blade members are open, the ratio of said first radius to said third radius is preferably 0.791.

* * * * *